United States Patent [19]

Al-Sioufi

[11] Patent Number: 4,675,159

[45] Date of Patent: Jun. 23, 1987

[54] METHOD AND DEVICE FOR DISINFECTING BIOLOGICAL FLUIDS AND CONTAINER FOR SAME

[76] Inventor: Habib Al-Sioufi, P.O. Box 654, Brookline, Mass. 02146

[21] Appl. No.: 780,668

[22] Filed: Sep. 29, 1985

[51] Int. Cl.⁴ .................. B65D 81/20; A61B 5/14; A61J 1/00
[52] U.S. Cl. .................................. 422/36; 422/102; 210/764; 210/927; 210/516; 128/764; 436/166
[58] Field of Search ................ 422/36, 102, 61; 210/516, 927, 764, 787; 128/764, 765; 436/166

[56] References Cited

U.S. PATENT DOCUMENTS

| | | | |
|---|---|---|---|
| 3,901,219 | 8/1975 | Kay | 128/764 |
| 4,189,382 | 2/1980 | Zine, Jr. | 210/927 |
| 4,294,707 | 10/1981 | Ikeda et al. | 210/927 |
| 4,308,232 | 12/1981 | Crouther et al. | 210/927 |
| 4,336,880 | 6/1982 | Mehl | 422/102 |

FOREIGN PATENT DOCUMENTS

| | | | |
|---|---|---|---|
| 2463621 | 4/1981 | France | 422/36 |
| 54-105877 | 8/1979 | Japan | 128/764 |

*Primary Examiner*—Benoit Castel
*Attorney, Agent, or Firm*—John S. Hale

[57] ABSTRACT

A technique and receptacle for disinfecting biological fluids such as whole blood is described in which the disinfectant is prepositioned in a receptacle for biological fluids utilized for clinical evaluation in an amount which is sufficient to disinfect the fluid without interfering with subsequent clinical evaluation. The invention is specifically directed to disinfecting viral contaminants in blood by providing a closed container for the blood specimen which contains an amount of an aldehyde based disinfectant such as glutaraldehyde sufficient to destroy without otherwise affecting the integrity of the specimen for future evaluation. The amount of aldehyde based disinfectant positioned in the container is adjusted to provide an ultimate concentration in the blood specimen of aldehyde of about 0.1 to 2.5 weight percent and is buffered to a pH of about 7.2 to 8.5 percent preferably about 7.4. To increase the stability and shelf life of the sample container and disinfectant, activation or buffering to the indicated pH range does not take place until or just prior to introduction of the specimen into the container. In a particularly preferred embodiment of the invention, the closed sample container is evacuated and provided with an elastomeric stopper adapted to receive the hollow needle of a syringe whereby the blood specimen is introduced into the container directly from the donor.

27 Claims, 12 Drawing Figures

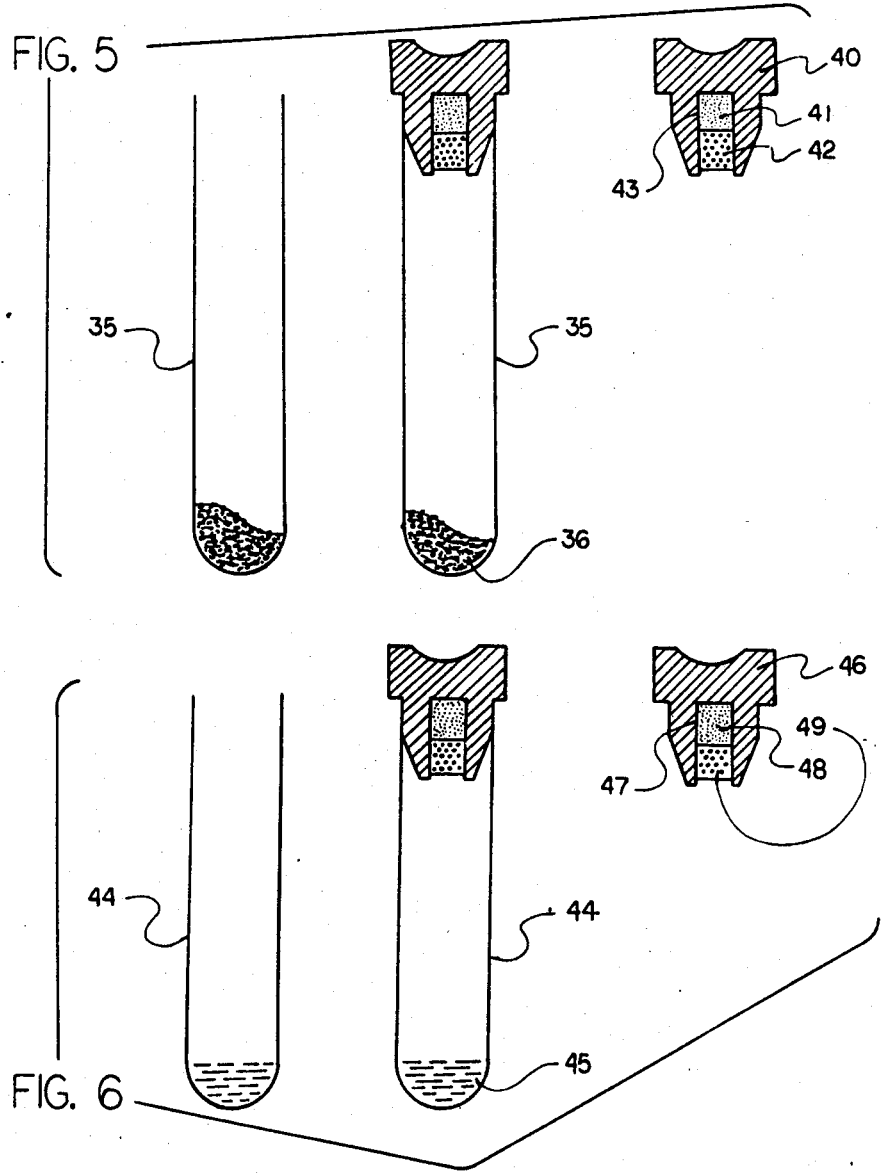

METHOD AND DEVICE FOR DISINFECTING BIOLOGICAL FLUIDS AND CONTAINER FOR SAME

SUMMARY OF THE INVENTION

The present invention is directed to a device and method for combating and destroying biological contamination in specimens of biological fluids such as blood intended for medical evaluation without interfering with the integrity of the proposed evaluation. More specifically, the present invention is particularly concerned with disinfecting viral contamination in biological specimens to avoid infecting those coming in contact either with the specimen itself or the receptacles and equipment used to contain and evaluate the specimen. Of particular concern in the present invention is the avoidance of contamination by HTLV-III Virus responsible for Acquired Immune Deficiency Syndrome and Hepatitis Virus which may be present in blood specimens drawn for medical evaluation.

BACKGROUND OF THE INVENTION

The incidence of hospital acquired infections has been increasing in recent years at an alarming rate which has caused great concern among the staffs of hospitals and especially those working in the laboratories. While many disinfection and sterilization techniques have been employed to alleviate this problem in different functional sections of the hospital, these techniques have not consistently provided a safe environment for the staff. Frequently, the disinfection and sterilization techniques which have been used have been employed after overt contamination has taken place such as spilling, broken samples, etc. While these techniques have helped to reduce the incidence of laboratory acquired infections, they have not curtailed them. With the increasing incidence of contagious pathogens that can be tramitted by patient's specimens, especially blood and particularly such dangerous contaminants as the AIDS and hepatitis viruses, a new and safer technique for handling laboratory specimens is needed.

Various disenfectants and sterilizing agents have been employed with varying degrees of success, both in hospitals and other environments. Monoaldehydes such as formaldehyde have been used successfully as a disinfectant, however, dialdehydes, paticularly glutaraldehyde, have been more preferred. Examples of glutaraldehyde-based disinfectants are a dilute sodium phenate-flutaraldehyde solution buffered to pH 7.4, an activated solution which contains 2.0% glutaraldehyde buffered to pH 7.5–8.0 and a disinfectant and sterilizing solution containing 2% glutaraldehyde at pH 7.0–7.5.

The extensive use of glutaraldehyde based compositions as an antiseptic and disinfectant has led to extensive studies of the compound and its activity. Glutaraldehyde has been classified as a chemosterilizer and has been defined by Borick, *J. of Pharm. Sciences*, vol. 53, no. 10, October, 1964, as a chemical agent capable of destroying all forms of microbiol life including bacterial and fungus spores, tubercle bacilli and viruses. The compound has in fact been shown to be effective against a wide range of viruses even in the presence of high levels of organic matter which tend to destroy the potency of other disinfectants. The degree of biocidal activity observed in glutaraldehyde solutions is very much dependent on the pH of the solution as enhanced biocidal activity is found in alkaline solutions.

Boucher et al., *Proc. West Pharmacal Soc.* 16, pp.282–288, 1973, postulated that the biocidal activity of qlutaraldehyde is controlled by the distance between the aldehyde groups and their tendency to polymerize thereby allowing free aldehyde groups to interact with the amino groups of the bacterial cell. This agrees with the findings of Rubbo et al., *J. Appl. Bacteriol* 30, pp.78–87, 1967, that antibacterial activity is due to the two aldehyde groups present on the molecule. After considering these results, Navarro and Monsan, *Ann. Microbiol* 127B, pp.295–307, 1976, concluded that only structures containing two aldehyde groups allow formation of an aldol type polymer at an alkaline pH, and also produces a similar sterilizing effect at acid pHs on the increasing concentrations. In other words, while the extent of polymerization is considerable at alkaline pHs, it is negligible in acid solutions unless the concentration is increased. On the other hand, acid solutions at pH3-4 of glutaraldehyde are considerably more stable than alkaline solutions.

The antimicrobial acitivity in any compound can not be viewed in isolation but must be described with reference to a number of factors including pH, temperature, organic matter present, and concentration. For glutaraldehyde, it has been common to use a 2% solution at room temperature and an alkaline pH of about 7.9. Unfortunately, alkaline solutions of glutaraldehyde are much less stable than acid solutions owing to the polymerization reactions already described, with a corresponding loss of antimicrobiol activity. A reduction in sporicidal activity of activated glutaraldehyde on storage has been observed in reports of Kelsey et al., *J. Clin. Pathol.* 27, pp.632–638, 1974, Thomas and Russell, *J. Appl. Microbiol* 28, pp.331–225, 1974b, Gorman and Scott, *Int. J. Pharma* 4, pp.57–65, 1979a. This reduction in sporicidal activity is directly related to a drop in concentration of the free aldehyde which appears to be essential for biological activity. Borick, *Adv. Appl. Microbiol* 10, pp.291–312, 1968, has estimated that glutaraldehyde concentration actually falls from 2.1% at pH 8.5 to 1.3% at pH 7.4 over a period of twenty-eight days at ambient temperatures. Accordingly, it has generally been the practice to employ glutaraldehyde as a 2% solution to which an activator is added to bring the pH to approximately 8 at the time of use. Such a solution used at room temperature will, for example, disinfect within 10 minutes and sterilize within 10 hours. However, it has been recommended that this solution be discarded after 14 days because of the significant decrease in activity and free aldehyde concentration. This instability has led to the development of more stable preparations formulated at lower pHs and some with other potentiators included to increase the otherwise low level of activity observed at lower pH.

The inevitable conditions of clinical use for disinfection and sterilization frequently means that organic matter is present such as blood and pus. This organic matter can act either by protecting the microbial species from antimicrobial attack or by competing with the microbial cell for active sites on the disinfectant molecules, thus reducing the effective concentration of disinfectant substance. Accordingly, many otherwise effective disinfectants and sterilizing agents may become ineffective where organic material, such as blood, is contacted. Glutaraldehyde, however, has a high resistance to neutralization by organic matter. Borick et al,

*J. Pharm. Sci.* 53, pp.1273–1275, 1964, for example has reported that the presence of 20% blood serum did not appear to adversely effect the activity of glutaraldehyde while Snyder and Cheatle, *Am. J. Hosp. Pharm.* 22, pp.321–327, 1965, have reported that 1% whole blood did not effect glutaraldehyde activity.

One of the most important considerations in selecting a suitable disinfectant, in addition to its potency and sustained effectiveness as a disinfectant, is the toxicity of the composition to individuals coming in contact with it. Various studies have shown that glutaraldehyde, in moderate effective concentrations, is generally only slightly irritating to the skin, mucous membranes and eyes. Sato and Dobson, *Arch. Dermatol* 100, pp.564–569, 1969, have found that 5% glutaraldehyde was only irritating if the epidermal barrier was not intact.

Aqueous solutions of glutaraldehyde have been used to treat hyperhydrosis and it has been used topically in the treatment of onychomycosis. Prevention of dental calculus formation and reduction of dental cavity formation in the mouth has been achieved by using oral compositions incorporating glutaraldehyde. In the cosmetic field, glutaraldehyde has been proposed for disinfection of production equipment and as a preservative. Glutaraldehyde has been used as a disinfectant for control of mastitis.

Accordingly, glutaraldehyde is now a generally accepted disinfectant and is found in a number of commercial preparations for disinfection and sterilization. Babb et al., *J. Hosp. Infec.* 1, pp.63–75, 1980, for example, have compared nine glutaraldehyde products.

Glutaraldehyde has also been used extensively in various non microbiological areas including the leather tanning industry and tissue fixation for electromicroscopy. In microbiological areas, glutaraldehyde has been employed principally as a liquid chemical sterilizing agent for medical and surgical material that cannot be sterilized by heat or irradiation. Compared with other disinfectants, glutaraldehyde has been found to be superior for disinfection of face masks, breathing tubes and other respiratory therapy equipment. Important advantages of glutaraldehyde as a chemosterilizer are: its activity in the presence of organic material, non-corrosive action towards metals, rubber, lenses and most materials, and lack of deleterious effect on cement and lenses of endoscopes. Further, glutaraldehyde has been recommended for decontamination of dental, surgical instruments and working surface where the hepatitis B surface antigen may be present as well as for the treatment of warts.

From the above mentioned studies testing any biological specimen containing glutaraldehyde will not damage the instrument used in testing. Osterberg, *Arch. Pharm. Chemi. Sci. Ed.* 6, pp.241–248, 1978, found that damage to leukocytes was apparent only above a 100 microg/ml. glutaraldehyde level. In addition, no erythrocyte damage occurred at the glutaraldehyde concentrations used.

The use of aldehydes in electron microscopy was extensively studies and it was found that many cytochemical reactions can be performed on tissue specimens after aldehyde fixation. Glutaraldehyde is effective in preserving both prokaryotes and eukaryotes, including fragile specimens such as marine invertebrates, embryos, diseased cells and fungi. Glutaraldehyde stabilizes blood plasma with little shrinkage of blood clots (Chambers et al. 1968, arch. Pathol. 85,18). Tissue specimens can be left in this fixative for many hours without apparent deterioration. Presently, glutaraldehyde is the most efficient and reliable fixative for preservation of biological specimens for routine electron microscopy and the previously mentioned and available data indicate that proteins are not denaturated to any marked extent by fixation with glutaraldehyde (M.A. Hayat, Fixative for electromicroscopy, Academic Press, 1981). Similarly, glutaraldehyde fixed-erythrocytes remain sensitive to the hemagglutination and hemagglutination inhibition tests for arbovirus antigens and antibodies (Wolff et al. [1977] J. Clin Microbiol. 6.55). Differential staining of viable and nonviable cells with alcian blue is maintained after fixation with glutaraldehyde (Yip and Auerperg, 1972, In Virto 7, 323). From the above mentioned studies, glutaraldehyde will preserve the biological specimens without otherwise affecting the integrity of the specimen for future evaluation.

As set forth above, the handling of biological specimens such as blood after sampling, during storage and medical evaluation poses a particular hazard for those coming in contact with the specimens, especially where there is a possibility of AIDS (HTLV-III) or Hepatitis Virus being present. Despite the known effectiveness of disinfectants such as glutaraldehyde in destroying these viruses, their use has essentially been limited to the containers and equipment coming in contact with the fluid, and only after such contact has occurred and the fluid disposed of. What remains especially hazardous is the contaminated body fluids themselves, such as AIDS (HTLV-III) or Hepatitis infected blood, which are carriers of the infection from the time they are drawn from the donor. Accordingly, what is needed is a technique for destroying such viral contamination instantaneously when the sample is taken, but without effecting the specimens for further testing.

DISCUSSION OF THE PRIOR ART

U.S. Pat. No. 3,016,328 describes disinfecting with a sporicidal composition containing a $C_2$ to $C_6$ saturated dialdehyde, such as glutaraldehyde, and an alkalinating agent in either alcoholic or aqueous solution at a pH above 7.4.

U.S. Pat. No. 3,282,775 describes disinfecting with a sporicidal composition containing a $C_2$ to $C_6$ saturated dialdehyde preferably glutaraldehyde and a cationic surface active agent.

U.S. Pat. No. 3,708,263 describes sterilizing at temperatures below 75° C. by contacting the equipment to be treated with an aqueous solution at pH 2 to 8.5 containing glutaraldehyde and DMSO simultaneously with ultrasonic wave energy.

U.S. Pat. Nos. 3,912,450; 3,968,248; and 3,968,250 describe disinfection or sterilization compositions that contain nonionic and anionic surfactants with aqueous or alcoholic glutaraldehyde solutions.

U.S. Pat. No. 4,093,744 describes sporicidal compositions containing glutaraldehyde at pH 6.5 to 7.4 which may contain a detergent and also a monoaldehyde.

U.S. Pat. No. 3,983,252 describes disinfectant compositions that contain a dialdehyde and an alkaline metal salt of a hydrocarbon carboxylic acid in aqueous solution and optionally an alcohol of up to seven carbon atoms or a diol with up to 4 carbon atoms such as ethylene glycol, propylene glycol, butylene glycol and/or a triol glycerol. The compositions are described as having improved stability in the pH range of 6 to 7.4.

U.S. Pat. No. 4,103,001 describes a sterilizing composition containing glutaraldehyde, a phenol and a metal phenate as active ingredients. The composition may also contain a humectant such as glycerol, propylene glycol or diethylene glycol.

U.S. Pat. No. 4,436,754 describes a disinfectant and sterilizing composition having low odor and irritation potential which is an aqueous solution containing a 2 to 6 carbon atom dialdehyde and may also contain formaldehyde and a diol of mono-substituted diol. Such compositions can be used at a pH of 2 to 9.

U.S. Pat. No. 3,886,269 describes a formaldehyde based disinfectant formed by passing formaldehyde gas through a solvent such as dimethyl sulfoxide or dimethyl formamide to form a gel-like polymer. The disinfectant described exhibits disinfection properties against bacterial vegetative cells, bacterial spores, and soil organisms.

U.S. Pat. No. 4,048,336 describes the use of a combination of glutaraldehyde and a monoaldehyde such as formaldehyde to kill spores on instruments.

M.A. Hayat in *Fixation for Electromicroscopy*, Academic Press, 1981, pages 64 to 147 describes fixative agents for preserving and fixing blood and/or tissue specimens.

Seymour S. Block in *Disinfection, Sterilization and Preservation*, Lea and Febiger, 1983, Chapters 2, 3, 9 and 22 describes sterilization techniques using glutaraldehyde and phenolic compounds.

DESCRIPTION OF THE INVENTION

In accordance with the present invention, a disinfectant for viral and other contamination in biological fluids such as blood is provided in a container for the biological fluid in an amount which is effective to destroy the contamination without otherwise compromising the integrity of the fluid specimen with regard to subsequent biomedical evaluation. The present invention is particularly adapted for use with evacuated containers into which freshly drawn specimens of blood are introduced and held for subsequent study. Such containers typically consist of a cylindrical tube having one open end into which an elastomeric stopper is fitted which is capable of accepting a hollow syringe needle to permit introduction of the bioligical fluid into the tube. Vessels of this sort are commercially available under the name Vacutainer Systems from Becton-Dickinson for example and are evacuated to provide a partial vacuum and provided with a hollow syringe needle which is disposed so that blood is drawn from the donor into the tube by the force of the vacuum in the tube.

According to the invention, the receptacle for receiving and holding the specimen of a biological fluid such as blood is provided with a disinfectant prior to introduction of the biological fluid in an amount sufficient to destroy viral contamination in the fluid and the receptacle without compromising the integrity of the specimen for medical evaluation. The disinfectant is preferably a mono or dialdehyde such as either glutaraldehyde or formaldehyde or a combination thereof, with the glutaraldehyde being the most preferred. The effective concentration of glutaraldehyde according to the invention is about 0.1 to 2.5 weight percent, preferably 0.13 to 2.0 weight percent based upon the total quantity of biological fluid to be placed in the receptacle. Thus, the actual amount of the glutaraldehyde present in the receptable before introduction of the fluid will depend on the size of the receptacle and the extend to which it is to be filled with fluid since the fluid is, in effect, the principal diluent. Lesser concentrations of glutaraldehyde will have a diminished effectiveness in destroying viral contamination while higher than 2.5% concentrations can effect biomedical evaluation of the fluid. Additional aldehydes such as fomaldehyde can also be used with the dialdehyde in amounts of about 0.1 to 3 percent by weight based on the total biological fluid. Where glutaraldehyde is the disinfectant employed in accordance with the invention, it is desirable to maintain a slightly alkaline pH of preferably about 7.2 to 8.5 preferably 7.4 in order to achieve maximum effect against viral contaminants.

As demonstrated in the prior art, however, glutaraldehyde undergoes increasing polymerization at alkaline pHs and the glutaraldehyde should be maintained at acid pH until just before use. While the receptacle can be provided with an alkalinating agent such as sodium bicarbonate, sodium phenate, lower alkanols, phenol or quaternary ammonium compounds which is isolated from the glutaraldehyde until just before introducing the biological fluid, it is preferred according to the invention to increase the pH of the glutaraldehyde by introduction of the blood specimen itself which has a pH of about 7.4 normally. Where buffering to a higher pH is required, suitable amounts of alkalinating agent can be used.

It is also desirable to incorporate into the receptable of the present invention effective amounts of substances to increase the permeability of the cell membrane to allow the disinfectant to reach intracellular pathogens more quickly. Such substances are dimethyl sulfoxide, and glycerol, either along or in combination. Additionally, other substances whose use in connection with sampling and testing of biological fluids, such as blood, is known can be used such as anticoagulants, preservatives and biocidal agents. By employing the various configurations which are embodiments of the present invention, activation of the disinfectant can take place prior to, during or after introduction of the specimen and the disinfectant can be released either before, during or after the specimen is introduced. The present invention will however be more fully appreciated by having reference to the drawings.

BRIEF DESCRIPTION OF THE DRAWINGS

FIG. 5 illustrates an embodiment of the present invention also similar to that of FIGS. 1 and 4 in which the stopper contains activator and disinfectant separated from each other.

FIG. 6 illustrates an embodiment similar to that of FIG. 5 having an anticoagulant rather than an inert barrier material.

DETAILED DESCRIPTION OF THE DRAWINGS

Figure 1:
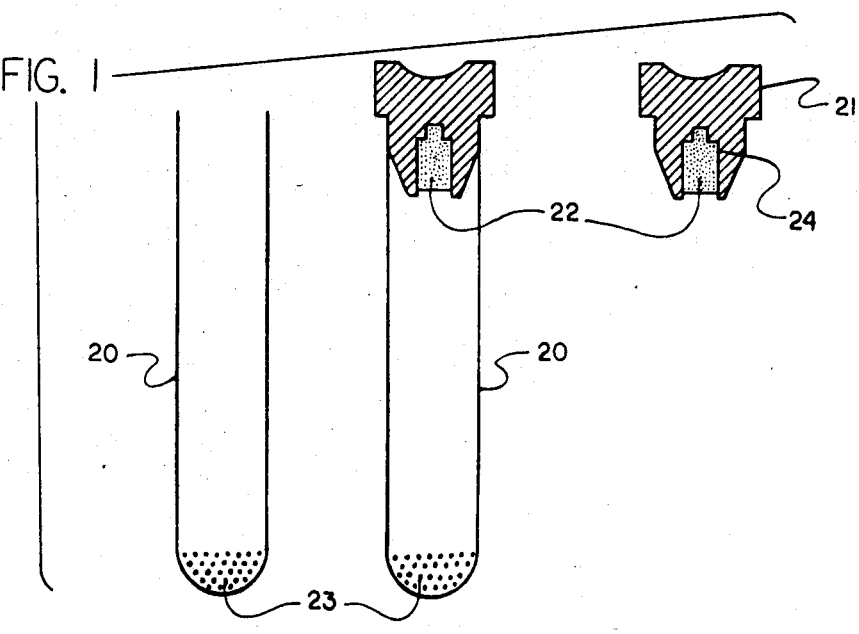
FIG. 1 illustrates one embodiment of the invention in which a closed tube is used having a stopper in one end and containing a disinfectant and activator.

Directing attention to the drawings, FIG. 1 illustrates an embodiment of the present invention in which a cylindrical tube 20 closed at one end is provided with an elastomeric stopper 21 at the other end. As previously noted, closed stopper tubes of similar construction are commonly employed for collecting samples of blood. It is frequently the case that these tube are provided with a partial vacuum and a double ended hollow syringe needle placed in the stopper end so that the blood sample can be drawn directly from the donor into the tube using the vacuum in the tube. Although the details of construction of these syringe devices is not herein illustrated since they are well known in the art, it will be understood that they can be used in connection with the present invention. In accordance with the embodiment of the invention shown in FIG. 1, a disinfectant material 23 is predisposed in the bottom of the tube 20 and a suitable alkaline activator 22 such as sodium bicarbonate is provided in a cavity 24 of the stopper 21. The two materials are thus kept separate from one another until the blood sample is introduced through the stopper into the tube whereby the mixing of the glutaraldehyde and activator takes place. It will be understood that the amount of glutaraldehyde present in the bottom of the tube 20 will depend upon the size of the tube and the quantity of blood to be drawn into the tube and should be sufficient to insure a concentration of between 0.1 and 2.5% glutaraldehyde once the blood sample is in the tube. The amount of activator present in the stopper cavity 24 will be sufficient to insure that the specimen and glutaraldehyde have an alkaline pH between 7.2 and 8, preferably about 7.4.

Figure 2:
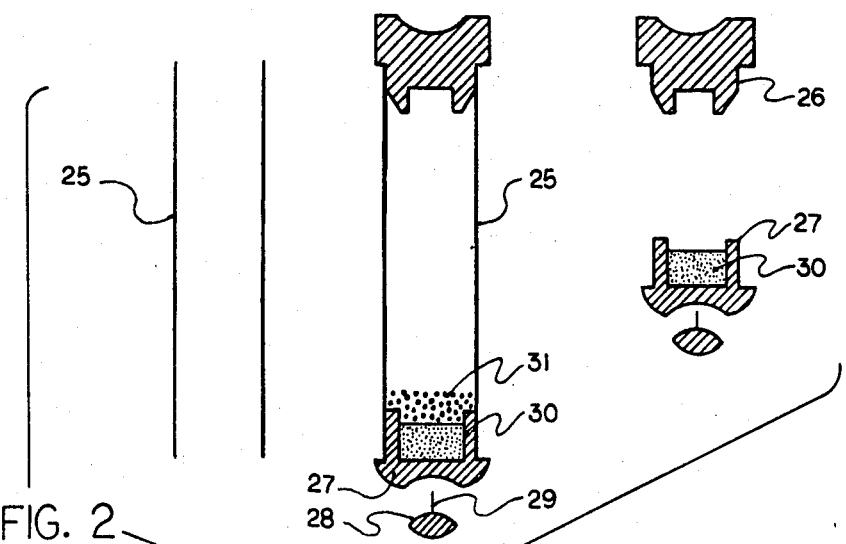
FIG. 2 illustrates an additional embodiment of the present invention whereby both ends of the tube are stoppered and one stopper is provided with the disinfectant or activator.

In the embodiment of the invention shown in FIG. 2, the cylindrical tube 25 is provided with a stopper at either end. The lower end of the tube 25 is closed by elastomeric stopper 27 having a recess which contains an activator such as sodium bicarbonate 30 which is separated by thin membrane from glutaraldehyde disinfectant 31 which is disposed freely in the tube. The other end of the tube is closed by stopper 26. A sharp pin 29 having a head 28 is provided for piercing the membrane separating the activator and disinfectant before or once the blood sample has been introduced into the other end of the tube 25 through stopper 26.

Figure 3:
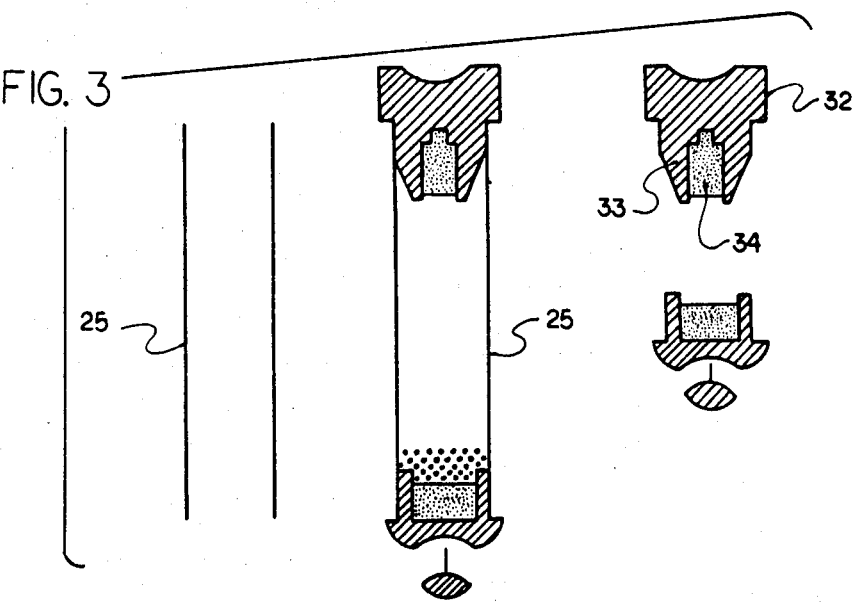
FIG. 3 illustrates an embodiment of the present invention similar to that of FIG. 2 in which one stopper contains anticoagulants.

FIG. 3 of the drawings illustrate an embodiment of the invention similar to that of FIG. 2 except that the upper end of the tube 25 is provided with a stopper 32 having a recessed area 33 provided with an anticoagulant 34 separated from the disinfectant to maintain the fluidity of the blood sample. Introduction of the blood sample through the stopper 32 releases the anticoagulant by rupturing a barrier to allow it to mix with the blood sample, disinfectant and activator which are released by the means of a pin.

Figure 4:
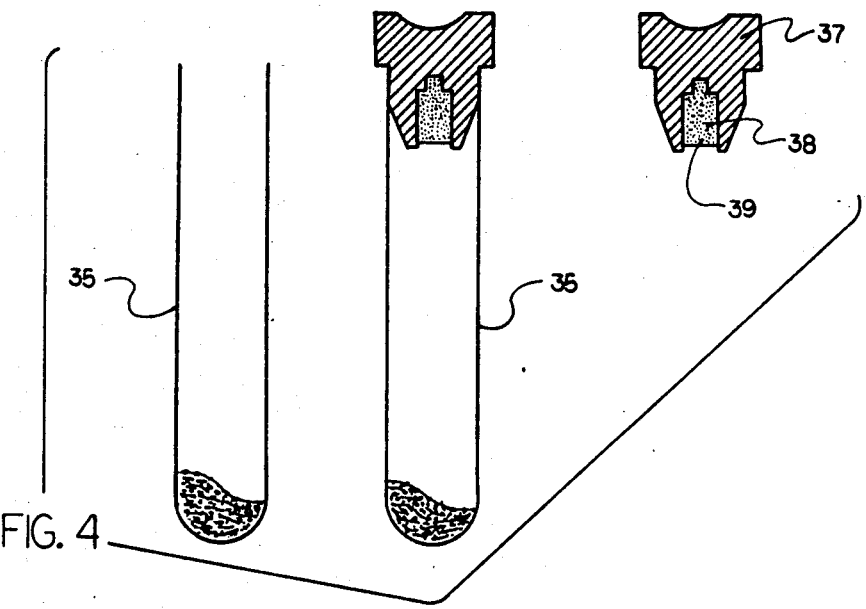
FIG. 4 illustrates an embodiment of the present invention similar to that of FIG. 1 except for the presence of an invert barrier material.

In FIG. 4 of the drawings, an embodiment of the invention otherwise similar to that of FIG. 1 is illustrated in which an activator 39 is provided in the cavity 38 of stopper 37 in the top of the tube. The glutaraldehyde disinfectant is however mixed with an inert barrier material and placed at the bottom of the tube 36. In this manner, activation of the glutaraldehyde to the appropriate pH will not occur until the blood sample is centrifuged to produce a separation of the serum.

In FIG. 5 of the drawings, the stopper 40 is provided with a recess 43 containing the activator 41 and disinfectant material 42 which are separated from one another by a thin membrane and from the inside of the tube. Inert barrier material is provided at the bottom of the tube 36.

The embodiment of the invention shown in FIG. 6 is similar to that of FIG. 5 except that the inert barrier material is replaced with an anticoagulant 45.

Figure 7:
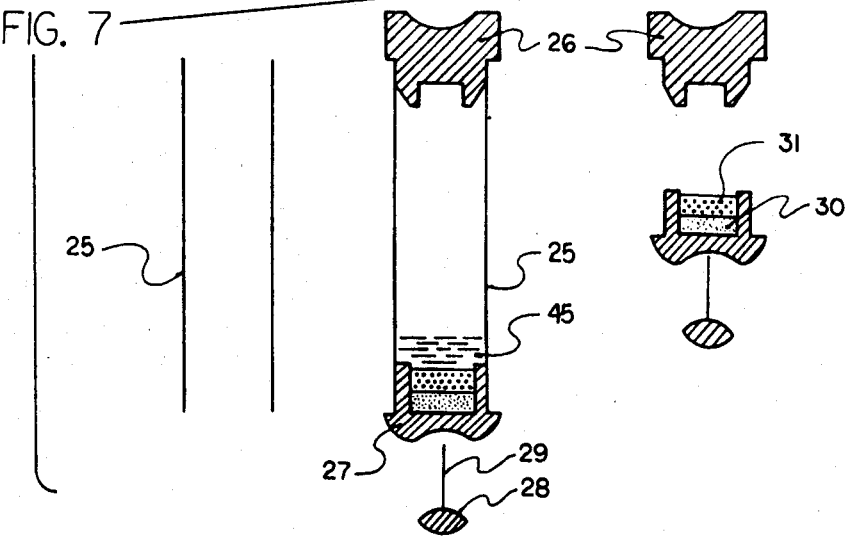
FIG. 7 illustrates an embodiment of the present invention having a tube similar to that of FIG. 2 in which one stopper contains activator and disinfectant separated from each other and containing anticoagulant.

FIG. 7 of the drawings illustrates an additional embodiment of the invention whereby stoppers are provided at both ends of the tube 25. The stopper 26 closing the lower end of the tube is provided with an activator at 30 and disinfectant 31 separated from one another by a thin membrane and from the inside of the tube. Anticoagulant 45 is placed in the tube directly over the stopper and disinfectant material. A pin 29 with head 28 is available to puncture the separating membranes to permit the materials to mix with the blood introduced through stopper 26 at the other end of the tube.

Figure 8:
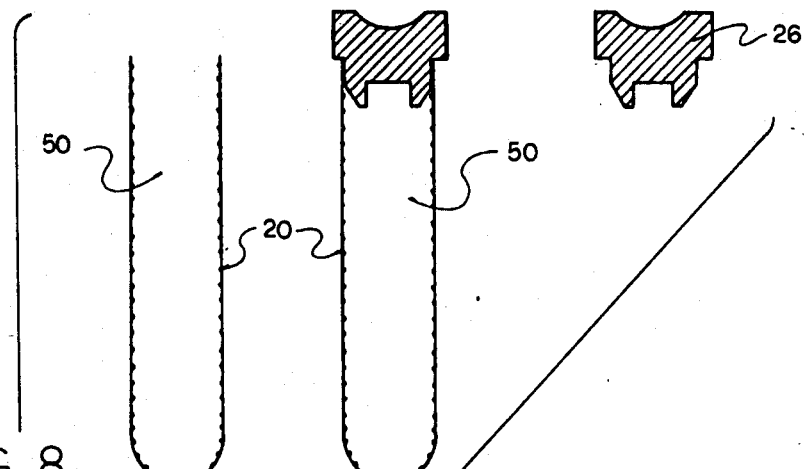
FIG. 8 illustrates an embodiment of the present invention having a tube similar to that of FIG. 1 but containing a disinfectant on the walls of the tube without activator.

FIG. 8 of the drawings illustrates a preferred embodiment of the invention in which disinfectant material 50 is coated on the inside of the tube 20 to provide a layer. The upper end of the stop of the tube 20 is closed by stopper 26 but no additional activator is provided since the amount of disinfectant 50 is adjusted so that its pH will become slightly alkaline with the introduction of blood into the tube which also provides the necessary dilution to result in a concentration of 0.1 to 2% glutaraldehyde.

Figure 9:
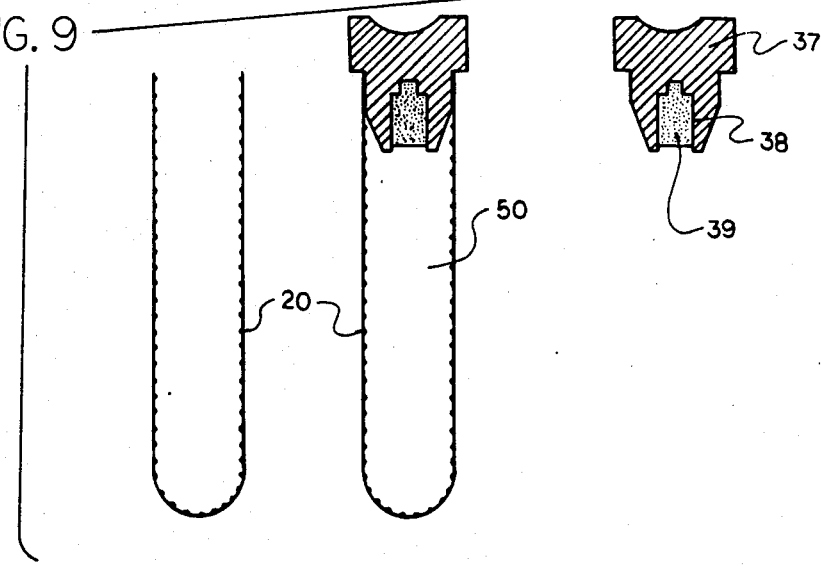
FIG. 9 illustrates an embodiment of the present invention similar to that of FIG. 8 except that activator is contained in the stopper.

In FIG. 9 of the drawings, an embodiment of the invention is shown similar to that of FIG. 8 in that the disinfectant material is a coating 50 on the inside of the tube 20. An activator such as sodium bicarbonate is provided and separated from the inside of the tube, however, in cavity 38 of stopper 37 at 39.

Figure 10:
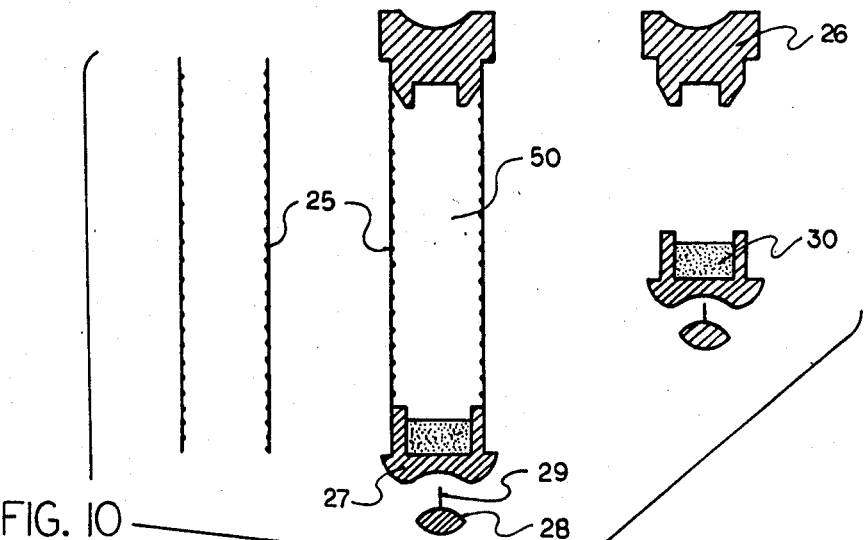
FIG. 10 illustrates an embodiment of the present invention similar to that of FIG. 2 but with disinfectant on the inner walls of the tube.

FIG. 10 of the drawings illustrates the embodiment of the invention whereby the cylindrical tube 25 is closed at both ends by respective stoppers 26 and 27. The stopper 27 is however provided with activator 30 which is separated from the inside of the tube and released into the tube to interact with the disinfectant 50 by inserting the pin 29 into the stopper 27 to rupture a membrane that separates the activator from the interior of the tube.

Figure 11:
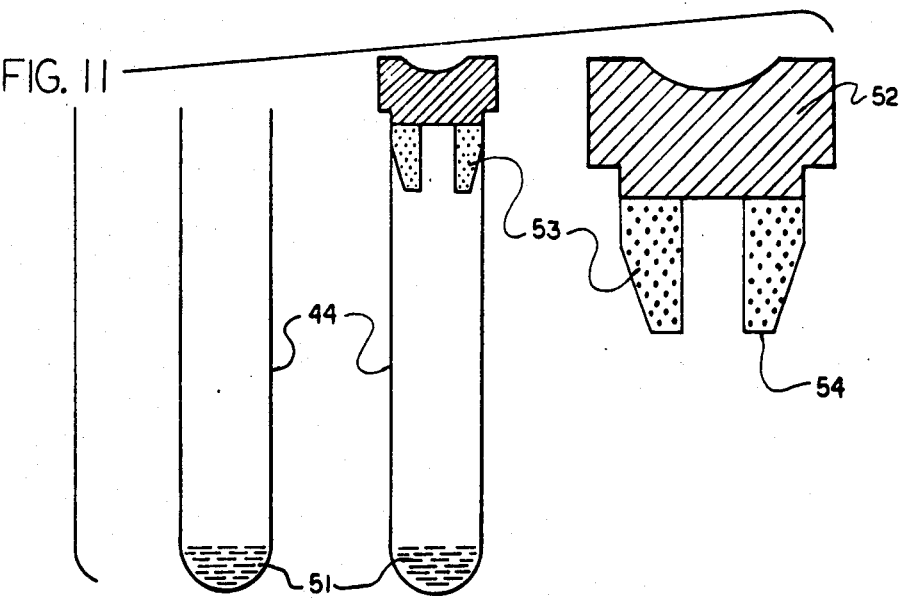
FIG. 11 illustrates an embodiment of the present invention in which a stopper is used which contains disinfectant and having a permeable membrane.
Figure 12:
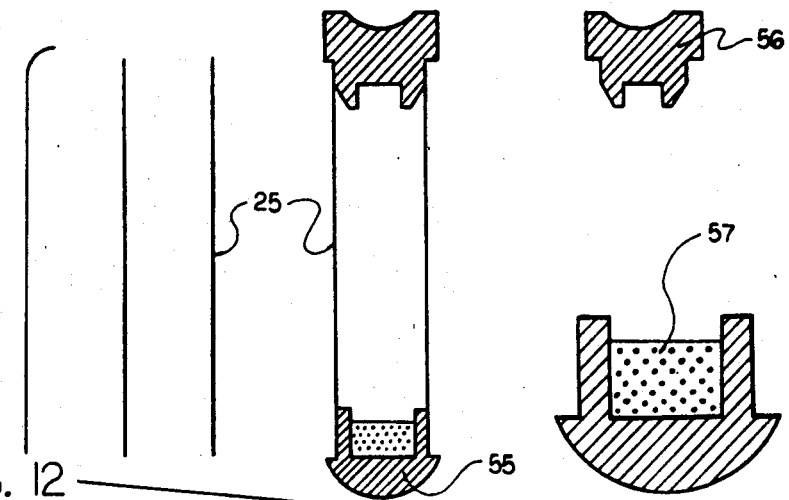
FIG. 12 illustrates an embodiment of the invention similar to that of FIG. 2 except that no activator is used in connection with the disinfectant and a stopper is used having a permeable membrane.

In FIG. 11 of the invention, either an anticoagulant or activator 51 is provided in the bottom of the tube 44. A porous material container 54 is provided on stopper 52 to hold the disinfectant 53 and permit it to diffuse through a permeable membrane into the tube 44 once the fluid specimen has been introduced into the tube and the tube inverted. In FIG. 12 of the drawings, the disinfectant material 57 is provided in an appropriate cavity in stopper 55 closing one end of the tube while stopper 56 closes the other end of the tube. A membrane prevents the disinfectant from entering the tube itself until blood is introduced, at which time the disinfectant diffuses through the membrane into the specimen.

It will be understood that while various preferred embodiments of the present invention have been described herein in order to illustrate and disclose Applicant's invention, additional variations and applications of the present invention are considered to fall within the scope thereof.

What is claimed:

1. An evacuated receptacle for holding a specimen of biological fluid for clinical evaluation, comprising a vessel closed at one of its ends by an elastomeric stopper adapted to be penetrated by means for introducing said specimen therein, said vessel also containing prior to introduction of said specimen about 0.1 to 2.5 weight percent based on the total fluid and disinfectant of a disinfectant for viral infection present in the specimen which disinfectant is one or more compounds or mixtures thereof selected from the group consisting of glutaraldehyde and formaldehyde said disinfectant being buffered substantially at the time said biological fluid is introduced therein to a pH of about 7.2 to 8.5.

2. The receptacle of claim 1 in which said vessel also contains an activator for said disinfectant.

3. The receptacle of claim 1 wherein both ends of said vessel are closed by elastomeric stoppers.

4. The receptacle of claim 3 wherein both of said stoppers are provided with cavities adapted to retain material until said biological fluid is introduced into said receptacle, the stopper adapted for penetration by said means for introducing the fluid being also adapted to release said material retained therein on penetration, and the other of said stoppers being provided with separate means to release material contained therein into said receptacle.

5. The receptacle of claim 4 wherein the material retained in one of said stoppers is said disinfectant.

6. The receptacle of claim 5 wherein said disinfectant is glutaraldehyde and said biological fluid is blood, said glutaraldehyde being present in an amount such that introduction of said blood dilutes its concentration to about 0.1 to 2.5 weight percent based on the combined blood and glutaraldehyde.

7. The receptacle of the claim 5 wherein an alkaline buffering agent is also retained in one of said stoppers in an amount sufficient to adjust the pH of the blood in said receptacle to about 7.2 to 8.5.

8. The receptacle of claim 4 wherein said means to release material into the receptacle is an externally provided means for penetrating an envelope or barrier confining said material within said other stopper.

9. The receptacle of claim 8 wherein said penetration means is a pin.

10. the receptacle of claim 1 wherein said disinfectant is disposed in the end of said vessel remote from said stopper.

11. The receptacle of claim 10 wherein the concentration of said disinfectant is about 0.13 to 2.0 weight percent.

12. The receptacle of claim 1 wherein said disinfectant is coated onto the inside walls of said vessel.

13. The receptacle of claim 1 which also contains an effective amount of anticoagulant for said blood.

14. The receptacle of claim 1 which also includes an effective amount of a substance or substances to enhance cell permeability selected from the group consisting of dimethyl sulfoxide and glycerol.

15. The receptacle of claim 14 wherein an alkaline buffering agent is disposed therein and separated from said glutaraldehyde prior to introducing said biological fluid, in an amount sufficient to accomplish said buffering when said fluid is introduced into the receptacle.

16. The receptacle of claim 15 wherein either said disinfectant of said buffering agent is disposed in a cavity in said stopper such that introduction of biological fluid through said stopper causes said disinfectant or agent to be released into said vessel and whichever of the agent or disinfectant is not disposed in said stopper is otherwise present in said vessel.

17. The receptacle of claim 15 wherein said buffering agent is selected from the group consisting of sodium bicarbonate, sodium phenate, alkanols or 2-4 carbons, phenol, and quaternary ammonium compounds.

18. The receptacle of claim 1 wherein said disinfectant is buffered to a pH of about 7.4 by introduction of a said biological fluid and said fluid is blood.

19. In an evacuated receptacle for receiving and holding a specimen of blood for clinical evaluation comprising a closed vessel provided with at least one elastomeric stopper to effect said closure, the improvement which comprises: said receptacle containing prior to introduction of the blood an effective amount of glutaraldehyde such that introduction therein of said blood results in a glutaraldehyde concentration of about 0.1 to 2.5 weight percent based on the total of blood and glutaraldehyde and a pH of about 7.2 to 8.5.

20. The receptacle of claim 19 wherein an alkaline buffering agent is disposed therein separate from said glutaraldehyde prior to introducing said blood therein in an amount sufficient to accomplish buffering of the blood and glutaraldehyde to a pH of 7.2 to 8.5.

21. The receptacle of claim 19 wherein said at least one elastomeric stopper is adapted to receive a hollow syringe needle for introducing said blood into said receptacle.

22. A method for destroying viral contamination in a specimen of biological fluid which comprises providing an evacuated container for said fluid having predisposed therein an aldehyde or mixture of aldehydes in an amount sufficient to be lethal to said viral contamination in the biological fluid to be placed in said container without otherwise interfering with subsequent biomedical evaluation of said specimen, said amount of aldehyde being present in said container in a concentration of about 0.1 to 2.5 weight percent based on the total fluid and aldehyde and a pH of about 7.2 to 8.5.

23. The method of claim 22 wherein said biological fluid is blood.

24. An evacuated receptacle for receiving and retaining a specimen of blood for clinical evaluation, comprising a closed, elongated cylinder having an elastomeric stopper closing at least one of its ends and adapted to receive and be penetrated by means for introducing said blood specimen into said cylinder; the interior of said cylinder being provided prior to introducing said blood specimen with an aldehyde disinfectant for viral contamination and preservation of said specimen in an amount sufficient for said disinfection but insufficient to effect clinical evaluation of said specimen, the amount of said aldehyde beinig further sufficient to insure a concentration of about 0.1 to 2.5 weight percent based on the combined sample and disinfectant and a pH of about 7.2 to 8.5.

25. The receptacle of claim 24 which also contains separate from the aldehyde an alkaline buffering agent in an amount sufficient to result in said pH of 7.2 to 8.5 on introduction of said blood specimen.

26. The receptacle of claim 24 wherein said aldehyde is glutaraldehyde.

27. The receptacle of claim 24 in which said aldehyde is a mixture of formaldehyde and glutaraldehyde.

* * * * *